United States Patent
Bozzoni et al.

(10) Patent No.: US 7,459,298 B2
(45) Date of Patent: Dec. 2, 2008

(54) PURIFICATION, CLONING AND BIOCHEMICAL CHARACTERIZATION OF XENDOU, ENDORIBONUCLEASIC ACTIVITY INVOLVED IN SMALL NUCLEAR RNA SPLICING-INDEPENDENT BIOSYNTHESIS IN XENOPUS LAEVIS

(75) Inventors: Irene Bozzoni, Rome (IT); Elisa Caffarelli, Rome (IT); Pietro Laneve, Rome (IT)

(73) Assignees: Universita'Degli Studi di Roma "La Sapienza", Rome (IT); Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 10/520,401

(22) PCT Filed: Jul. 4, 2003

(86) PCT No.: PCT/IT03/00424

§ 371 (c)(1),
(2), (4) Date: Sep. 12, 2005

(87) PCT Pub. No.: WO2004/005518

PCT Pub. Date: Jan. 15, 2004

(65) Prior Publication Data

US 2006/0084062 A1    Apr. 20, 2006

(30) Foreign Application Priority Data

Jul. 8, 2002    (IT)    .................... RM2002A0365

(51) Int. Cl.
| | |
|---|---|
| C12N 15/00 | (2006.01) |
| C07H 21/00 | (2006.01) |
| C12N 5/10 | (2006.01) |
| C12N 1/21 | (2006.01) |
| C12N 9/16 | (2006.01) |
| C12N 9/22 | (2006.01) |
| C12Q 1/44 | (2006.01) |
| C12P 21/00 | (2006.01) |
| C07K 14/00 | (2006.01) |

(52) U.S. Cl. .................... 435/199; 435/196; 435/320.1; 435/325; 435/252.3; 435/69.1; 536/23.2; 536/19; 530/350

(58) Field of Classification Search .............. 435/320.1, 435/325, 252.3, 69.1, 199, 19; 536/23.2; 530/350

See application file for complete search history.

(56) References Cited

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Laneve P.; "Purificazione e caratterizzazione di una nuova attivita endoribonucleolitica coinvolta nella biosisntesi dei piccoli RNA nucleolari in X. laevis"; Thesis (2001), Department of Genetics and Molecular Biology, University of Rome, Rome, Italy.
Caffarelli E. et al.: "A novel Mn++-dependent Ribonuclease that functions in U16 SnoRNA processing in X. laevis" Biochemical and Biophysical Research Communications, vol. 233, 1997, pp. 514-517.
Laneve P. et al.: "Purification, cloning, and characterization of XendoU, a novel Endoribonuclease involved in processing of intron-encoded small nucleolar RNAs in Xenopus laevis" The Journal of Biological Chemistry, vol. 278, No. 15, Apr. 11, 2003, pp. 13026-13032.
Database EMBL Jan. 27, 2001 Clifton S. et al.: "daa55d05.x1 Wellcome CRC pCS2+ st19-26 Xenopus laevis cDNA clone Image: 4059704 3'similar to SW: PP11_Human P21128 Placental Protein 11 Precursor; mRNA sequence" Database accession No. BG038970.
Caffarelli, E. EMBL accession No. AJ507315, Sep. 5, 2002.

* cited by examiner

*Primary Examiner*—Delia M Ramirez
(74) *Attorney, Agent, or Firm*—Young & Thompson

(57) ABSTRACT

Cloning and characterization of the gene for $Mn^{++}$ dependent RNA-sc endoribonucleasic activity able to generate 2'-3' cyclic phosphate and 5'OH ends.

4 Claims, 10 Drawing Sheets

C.

1) X. laevis oocyte nuclear extract    (ONE)

2) Ammonium sulphate fractionation

3) Hydroxylapatite chromatography 4) blue sepharose chromatography

5) Hydroxylapatite chromatography

6) Gel filtration chromatography

D.

1  2  3  4  5  6

```
                                                    M   A   S   N   R   G     6
         5'- attggggaactgggagcagagagtgacgggcaggagcc  ATG GCG AGT AAC AGG GGG Q   L   N   H   E   L   S   K   L   F   N   E   L   W   D   A   D   Q   N   R    26
CAG CTG AAC CAT GAA CTC TCC AAG CTG TTT AAT GAG CTG TGG GAC GCA GAT CAG AAC CGG M   K   S   G   K   D   Y   R   I   S   L   Q   G   K   A   G   Y   V   P   A    46
ATG AAG TCC GGG AAG GAT TAT CGG ATC TCC TTG CAG GGT AAA GCA GGG TAC GTA CCC GCC G   S   N   Q   A   R   D   S   A   S   F   P   L   F   Q   F   V   D   E   E    66
GGT TCC AAC CAG GCC AGG GAC AGC GCC TCG TTC CCG CTC TTC CAG TTC GTC GAT GAG GAG K   L   K   S   R   K   T   F   A   T   F   I   S   L   L   D   N   Y   E   M    86
AAG CTG AAG AGC AGG AAG ACG TTT GCA ACC TTC ATT TCC CTG CTG GAC AAT TAT GAG ATG D   T   G   V   A   E   V   V   T   P   E   E   I   A   E   N   N   N   F   L   106
GAC ACG GGG GTG GCC GAG GTT GTG ACT CCG GAG GAA ATC GCT GAA AAC AAC AAC TTC CTG
                                                         1
 D   A   I   L   E   T   K   V   M   K   M   A   H   D   Y   L   V   R   K   N   126
GAC GCC ATT CTG GAA ACC AAA GTG ATG AAG ATG GCA CAT GAC TAC CTG GTG AGG AAG AAC
                                                     2
 Q   A   K   P   T   R   N   D   F   K   V   Q   L   Y   N   I   W   F   Q   L   146
CAA GCC AAA CCC ACC CGG AAT GAC TTC AAG GTC CAA CTG TAC AAC ATC TGG TTC CAG CTG Y   S   R   A   P   G   S   R   P   D   S   C   G   F   E   H   V   F   V   G   166
TAC TCA CGG GCC CCA GGG AGC AGA CCC GAT TCG TGC GGC TTT GAG CAC GTG TTT GTG GGA E   S   K   R   G   Q   E   M   M   G   L   H   N   W   V   Q   F   Y   L   Q   186
GAA TCG AAG CGA GGG CAG GAG ATG ATG GGG CTT CAC AAC TGG GTC CAG TTT TAC CTT CAG E   K   R   K   N   I   D   Y   K   G   Y   V   A   R   Q   N   K   S   R   P   206
GAG AAG AGG AAG AAC ATC GAC TAT AAA GGA TAC GTG GCT CGG CAG AAC AAG AGT CGG CCG D   E   D   D   Q   V   L   N   L   Q   F   N   W   K   E   M   V   K   P   V   226
GAT GAA GAT GAT CAG GTG TTG AAC CTG CAG TTC AAT TGG AAG GAG ATG GTG AAA CCC GTC G   S   S   F   I   G   V   S   P   E   F   E   F   A   L   Y   T   I   V   F   246
GGC AGC AGC TTC ATT GGC GTC AGC CCG GAA TTC GAA TTC GCC CTT TAC ACC ATC GTC TTC L   A   S   Q   E   K   M   S   R   E   V   V   R   L   E   E   Y   E   L   Q   266
CTC GCG TCT CAG GAG AAG ATG AGC CGA GAA GTC GTT CGG CTG GAA GAA TAC GAA CTG CAG
                                             3
 I   V   V   N   R   H   G   R   Y   I   G   T   A   Y   P   V   L   L   S   T   286
ATC GTC GTC AAT CGC CAC GGC CGT TAT ATA GGG ACC GCC TAC CCC GTC CTC CTG AGC ACC N   N   P   D   L   Y   *                                                       292
AAT AAC CCG GAT CTG TAC TGA ggggcggggctagagatcacagccggttccacggtttgggtgcatt tactaacaaaactgcaccaatgcaacaacaatgcaagcagataatgggggcaggtccatatccctctgctttccc tagcgtgtgtggggcacattaaccctataactgtcactcactgcaccagaccccattatttaacccccacaagggac atcaagccagtgccttgttatgagagagcgcagccggggcttctctactgtgaaacttctgtattgcatagagtt tacttggtttcttcctccagacaatttcacttttttttttgctttgccttcaaccattaaaagtccatgacatttc tgt -3'
```

PURIFICATION, CLONING AND BIOCHEMICAL CHARACTERIZATION OF XENDOU, ENDORIBONUCLEASIC ACTIVITY INVOLVED IN SMALL NUCLEAR RNA SPLICING-INDEPENDENT BIOSYNTHESIS IN XENOPUS LAEVIS

Endoribonucleases play essential role in RNA metabolism participating both in "degradative" pathways, such as mRNA decay (Schoenberg and Chemokaiskaya, 1997), and in "maturative" pathways, to generate functional RNA molecules from primary transcripts. Only a few endoribonucleases have been isolated in eukaryotes, most of them being involved in biosynthesis of translation apparatus components. Among these, there are ribonucleoprotein enzymes, such as RNase P and RNase MRP, which act as site-specific endoribonucleases; RNase P is involved in generation of the 5' end of tRNAs (Nashimoto, 1995), whereas RNase MRP is implicated in processing of pre-rRNA (Lygerou et al., 1996). Other endonucleolytic activities, as 3'-tRNase, tRNA splicing endonuclease and members of RNase III family (Trotta et al., 1997; Bujnicki and Rychlewski, 2000; Zamore, 2001) are protein enzymes. 3'-tRNase is an eukaryotic spermidine-dependent endoribonuclease which precisely removes the 3'-end tail from tRNA precursors (Castano et al., 1985; Nashimoto, 1995). tRNAs splicing endoribonucleases are required for the intron removal from pre-tRNAs: it is an $Mg^{++}$-dependent enzyme and cleaves pre-tRNAs at 5' and 3' splice sites, releasing products having 2'-3' cyclic phosphate and 5'OH ends (Peebles et al., 1983) RNases III are endoribonucleases acting on double-strand RNA found in bacteria and eukaryotes: they were first isolated in *E. coli* (Court, 1993; Nicholson, 1997) and subsequently eukaryotic orthologs were identified on the basis of sequence similarity. *S. cerevisiae* RNase III (Rnt1p), was shown to be involved in several biosynthetic events such as pre-rRNAs, snRNAs and snoRNAs processing (Elela et al., 1996; Kufel et al., 1999; Chanfreau et al., 1997; Allmang et al., 1999; Chanfreau et al., 1998). Recently it was shown that Rnt1p is also involved in the release of the intron-encoded snoRNAs, U18 and snR38 from their pre-mRNAs (Giorgi et al., 2001). Furthermore, a new member of eukaryotic RNAses III family, named "Dicer", has been identified in metazoa (Bemstein et al., 2001). It is known to be involved in interference (RNAi) pathway, generating 21-23 nt small interfering RNAs (siRNAs) from longer partially double stranded precursors. These processing products act in RNA-mediated gene regulation (Ambros, 2001). Cleavage by Rnase III releases 3'OH and 5' phosphate ends and it is $Mg^{++}$-dependent.

The authors of the invention previously demonstrated that an endoribonucleolytic activity plays a key role in the biosynthesis of the box C/D U16 snoRNA, encoded in the third intron of the L4 ribosomal protein gene in *X. laevis* (Caffarelli et al., 1994). The authors already showed that U16 processing from the host intron is alternative to the splicing reaction: thereby, synthesis of the L4 mRNA is alternative to the production of U16 snoRNA (Caffarelli et al., 1996). In this context the biosynthetic mechanism of U16, per se, regulates the expression of L4 gene at the post-transcriptional level.

The authors now purified to homogeneity from *X. laevis* oocyte nuclear extracts (ONE) and characterized the endonucleolytic activity (XendoU, GenBank TM/EBI Data Bank AJ507315) responsible for the processing of U16 snoRNA from its host intron. Partial protein sequencing allowed to clone XendoU cDNA, to express it and to study features of the enzyme. This protein represents a novel endoribonucleasic activity, being: i) poly-U specific, ii) single filament specific, iii) $Mn^{++}$-dependent and iv) able to release cleavage products with 5' OH and 2'-3' cyclic phosphate ends.

Furthermore the protein represents an useful biotechnological tool showing additional advantages in comparison to known RNases like, for example, selective but non stringent substrate specificity and opportunity to obtain amounts of the recombinant protein.

Finally the inclusion of XendoU protein with endoribonucleasic activity in pharmaceutical kits containing other RNases already known for molecular analysis of nucleic acids, particularly RNA, or for the preparation of biological macromolecules, like, for example, c-DNA, genomic DNA, plasmids, recombinant proteins, allows to remedy to the limited number of commercially available Rnases and to increase selectivity and efficiency of said kits.

It is therefore an object of the present invention a nucleic acid encoding for a protein with endoribonucleasic activity which is poliU sequences and single filament specific, $Mn^{++}$-dependent and releases as cleavage products molecules having 2'-3' cyclic phosphate and 5'OH ends. Preferably nucleic acid includes substantially SEQ ID NO: 1 nucleotide sequence, functional homologs thereof or complementary sequence thereto.

It is a further object of the invention a recombinant vector able to express effectively the inventive nucleic acid in prokaryotes.

It is a further object of the invention a recombinant vector able to express effectively the inventive nucleic acid in eukaryotes.

Those skilled in the art will be able to recognize the most suitable vectors also considering the host organism in order to express the inventive nucleic acid.

It is a further object of the invention a protein with endoribonucleasic activity which is poly-U sequences and single filament specific, $Mn^{++}$-dependent and releases RNA molecules bearing 2',3' cyclic phosphate and 5'OH ends as cleavage products, or functional portions thereof. Preferably the protein is encoded by inventive SEQ ID NO: 1 nucleic acid, more preferably protein substantially has SEQ ID NO: 2 amino acid sequence. Advantageously the protein is produced by synthetic or recombinant route using methods known by those skilled in the art. It is a further object of the present invention the use of the protein with endoribonucleasic activity in analytical or synthetic applications. Particularly analytical applications can be selected from the group including RNA sequencing, point mutation detection, RNA molecular digital fingerprinting determination, RNA structural analysis, Rnase protection assays.

Among the synthetic applications of the protein with endoribonucleasic activity according to the present invention there is RNA degradation for the preparation of biological molecules and particularly c-DNA, plasmid DNA, genomic DNA and recombinant proteins.

A further object of the present invention is the use of the protein with endoribonucleasic activity for the preparation of pharmaceutical kits for molecular analysis of nucleic acids, particularly RNA and synthesis of biological macromolecules, particularly c-DNA, plasmid DNA, genomic DNA and recombinant proteins.

Therefore pharmaceutical kits, including the protein with endoribonucleasic activity according to the present invention, suitable for the molecular analysis of nucleic acids, particularly RNA and synthesis of biological macromolecules, particularly c-DNA, plasmid DNA, genomic DNA and recombinant proteins are object of the present invention.

The invention will be now described without any limitation thereof referring to experimental procedures wherein reference will be made to the following figures:

BRIEF DESCRIPTION OF THE DRAWINGS

FIG. 4 shows cDNA (SEQ ID NO: 1) and amino acid sequence (SEQ ID NO: 2) of XendoU. Nucleotides of the 5' and 3' untranslated regions are shown in small letters, nucleotides of the ORF in capital letters. Above each codon the corresponding amino acid is shown. The sequence portions determined by automated Edman degradation and mass mapping experiments (see "Experimental Procedures") are indicated by numbers 1, 2 and 3. The stop codon is identified by an asterisk. Numbers on the right side of diagram correspond to the amino acid residues. Underlined are the amino acid sequences identified by MALDI-mapping experiments.

EXPERIMENTAL PROCEDURES

Figure 1A:
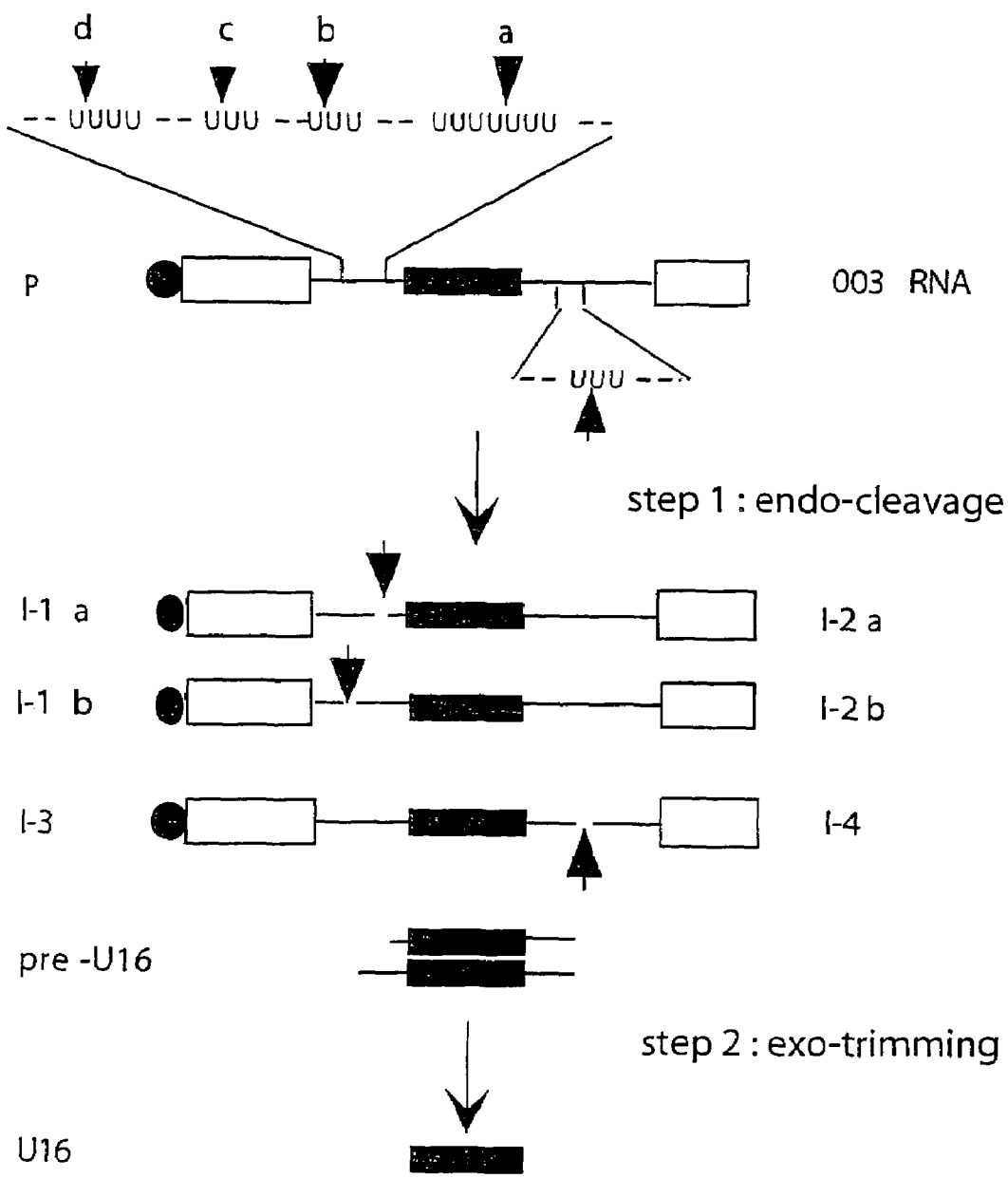
FIG. 1 shows activity assay and purification of XendoU. A, schematic representation of U16 snoRNA processing. P indicates U16-containing precursor (003 RNA); I-1a and I-1b represent the products generated by cleavage upstream from U16 while I-2a and I-2b represent their 3' complementary molecules thereto; 1-3 depicts the product originated from cleavage downstream from U16 while 1-4 represent its 3' respective complementary molecule; pre-U16 represents U16 precursor with additional 5' and 3' flanking sequences. Cap structure is shown as a black dot, exons as boxes, the intron as a continuous line and U16 snoRNA coding region as a thicker line. Large arrows localise the major sites of cleavage and small arrows the minor ones. B, in vitro U16 processing in unfractionated oocyte nuclear extracts (ONE) and with purified XendoU (XendoU). $^{32}$P-labelled 003 RNA was incubated for the times indicated below; RNA was then extracted and separated by 6% polyacrilamide-7M urea gel. The specific cleavage products are indicated aside. C, scheme of procedure employed for XendoU purification from ONE. D, proteins from the active fractions during the purification were separated on SDS-PAGE and visualised by Blue Coomassie staining. Numerals below refer to the corresponding purification steps schematised in panel C. The arrow points to the purified enzyme with an apparent molecular mass of 37 kDa.

Massive Isolation of Oocyte Germinal Vesicles and Nuclear Extract Preparation

*X. laevis* germinal vesicles were isolated following the procedure by Gandini-Attardi et al. (Gandini-Attardi et al., 1990) and the nuclear extracts were prepared as already described (Caffarelli et al., 1994).

Purification of XendoU Activity

XendoU was purified from oocyte nuclear extracts (ONE). ONE was fractionated by ammonium sulphate precipitation. Solid ammonium sulphate (280 mg/ml) was slowly added to the nuclear extract up to 45% saturation and the suspension was stirred for 30' at 4° C. and then centrifuged at 12.000 rpm for 30' at 4° C. The supernatant was made 70% saturated by a further addition of ammonium sulphate (240 mg/ml). The suspension was stirred and centrifuged as above. The resulting pellet was dissolved in ONE buffer (25 mM Hepes pH 7.5, 50 mM NaCI, 0.1 mM EDTA, 1 mM DTT, 10% glycerol) and then applied onto an hydroxyapatite column (CHT-II Econocolumn, Biorad). Column was washed with ONE buffer and then eluted with 5 column volumes of 100 mM Na-phosphate pH 7 in ONE buffer. The eluate was collected in 1 ml fractions next tested for the endonuclease activity. Selected fractions were pooled, diluted with 3 volumes of ONE buffer and applied on a Blue Sepharose column (Blue Sepharose Fast Flow Pharmacia). The column was washed with ONE buffer and then eluted with 5 column volumes of 0.2 M NaCl in ONE buffer. The eluate was then collected in 1 ml fractions; those displaying the specific activity were pooled and dialysed against ONE buffer. Protein mixture was subjected to a second fractionation on hydroxyapatite column. The elution was performed with 10 column volumes of a linear gradient 0-100 mM Na-phosphate pH 7 in ONE buffer. Collected fractions were tested and those with activity were pooled and concentrated by means of ultrafiltration device (CENTRICOM™ C10, Millipore). The concentrated fractions were then applied on a gel-filtration column (Pharmacia) previously equilibrated in ONE buffer. Elution was monitored collecting 0.5 ml fractions which were tested for specific activity.

Considering the yield of purified protein it can be assumed that XendoU represents no more than 1/1000 of the protein mass present in nuclear extract. To obtain enough protein for sequencing and characterization the described procedure was carried out on several ONE samples of 15-20 ml collecting together the final purified fractions.

Preparation and Isolation of Tryptic Peptides

Protein bands from SDS-PAGE analysis (5 µg) stained with Coomassie Blue R250 were excised, reduced with dithiothreitol and carboxamidomethylated. Gel pieces were equilibrated in 25 mM $NH_4HCO_3$, pH 8 and finally digested in situ with trypsin at 37° C. for 18 h. Peptides were extracted by sonication with 100 µl of 25 mM $NH_4HCO_3$/acetonitrile 1:1 v/v, pH 8 (twice). Peptide mixture was fractionated by reverse-phase HPLC on a VYDAC™ $C_{18}$ column 218TP52 (250×1 mm), 5 µm, 300 Å pore size (The Separation Group, USA) by using a linear gradient from 5% to 60% of acetonitrile in 0.1% TFA over 60 min, at flow rate of 90 µL/min. Individual components were manually collected and lyophilised.

Peptide Sequencing and Mass Spectrometry Analysis

Sequence analysis was performed using a PROCISE™ 491 protein sequencer (Applied Biosystems, USA) equipped with a 140C microgradient apparatus and a 785A UV detector (Applied Biosystems, USA) for the automated identification of PTH-amino acids.

Matrix assisted laser desorption ionization mass spectra were recorded using a Voyager DE-PRO mass spectrometer (Applied Biosystems, USA); an analytical mixture containing α-cyano-4-hydroxy-cinnamic acid was applied to the sample plate and allowed to be dried. Mass calibration was performed using the molecular ions from peptides produced by tryptic auto-proteolysis and the matrix as internal standards.

In Vitro RNA Synthesis and Oocyte Microinjection

U16-containing precursor (003 RNA), including the third intron of the L4 r-protein gene of *X. laevis*, was transcribed from plasmid 003 digested with HindIII (Caffarelli et al., 1994). U86-containing precursor was obtained as already described (Filippini et al., 2001). In vitro transcription reactions were performed in the presence of ($^{32}$P) αUTP as described (Caffarelli et al., 1998) and pre-mRNAs were injected into nuclei of stage V1 oocytes as already described (Caffarelli et al., 1994).

In Vitro Processing Reactions

ONE assay: as described by (Caffarelli et al., 1994).

XendoU assay: the reaction mixture (25 µl) contained $3\times10^4$ cpm of ($^{32}$P) labelled pre-mRNA, 6 mM $MnCl_2$, 50 mM NaCl, 25 mM Hepes pH 7.5, 1 mM DTT, 10 µg of *E. coli* tRNA, 20 U of RNAse inhibitor (PROMEGA) and 1 ng of purified XendoU. Reaction mixtures were incubated with RNA substrates at 24° C. for indicated times. The products of the reactions were analysed on 6% polyacrylamide-7M urea gels.

Substrate Specificity

The oligoribonucleotides

P1 (5'-GGAAACGUAUCCUUUGGGAG-3'), SEQ ID NO: 3;

P2 (5'-GGAAACGUAUCCUUGGGAGG-3'), SEQ ID NO: 4;

P3 (5'-GGAAACGUAUCCUCUGGGAG-3'), SEQ ID NO: 5;

P4 (5'-GGAAACGUAUCCUGUGGGAG-3'), SEQ ID NO: 6;

were 5' labelled: 10 pmol of each synthetic substrate were incubated at 37° C. for 30 min, in the presence of 10 units of Polynucleotide Kinase (Roche), and 10 µCi of ($^{32}$P)Y-ATP. The reaction was terminated at 65° C. for 5 min, primers were gel purified on 10% polyacrylamide-7M urea and incubated for 30 min in the presence of ONE or purified XendoU as described above. RNA was extracted and analysed on 10% polyacrylamide-denaturing gel. RNA ladder was obtained by incubation of P4 oligo (200.000 cpm) in 500 mM $NaHCO_3$ at 90° C. for 20 min.

Analysis of 3' Ends of Cleavage Products $^{32}$P-labelled and gel purified I-1 molecules (I-1a and I-1b generated by cleavages at the major sites a and b upstream from U16, see scheme of FIG. 1A), obtained in vitro after incubation of 003 RNA with ONE or XendoU, or in vivo after oocyte microinjection, were incubated in 10 µl of 10 mM HCl at 25° C. for 2 hours to open the cyclic phosphate as described by Forster (Forster et al., 1990). The phosphate was then removed by incubation of the RNA in 50 mM Tris-HCl pH 8.5, 0,1 mM EDTA in the presence of 1 U of calf intestine Alkaline Phosphatase at 50° C. for 60 min. The enzyme was inactivated by adding 1/10 volume of 0.2 M EGTA and the mixture heated at 65° C. for 10 min. RNA was extracted with phenol/chloroform and analysed on 10% polyacrylamide-7M urea gel.

Isolation of XendoU cDNA

A *X. laevis* stage 28 embryo cDNA library, constructed in λZAP II vector, was screened using a specific probe obtained by PCR amplification on *X. laevis* cDNA with degenerated oligonucleotides (MAHs 5'-ATGGCICAYGAYTAYYTIGT-3', SEQ ID NO: 7 and IGTa 5'-ACIGGRTAIGCIGTICCIAT-3', SEQ ID NO: 8) designed on peptides obtained by tryptic digestion of purified XendoU.

XendoU cDNA Expression in Reticulocyte Lysate

XendoU Open Reading Frame (ORF) was cloned into BLUE SCRIPT™ vector and $^{35}$(S)Methionine-labelled protein was produced by in vitro transcription and translation using the TnT-coupled Reticulocyte Lysate System Kit (PROMEGA™) according to the manufacturer's instructions. Translational products were analysed on 10% SDS-PAGE.

Primer Extension Analysis

In vitro transcribed U86-containing precursor was obtained from a standard T7 reaction, but in the presence of 500 µM unlabelled UTP. The transcript was injected into *X. laevis* oocytes or incubated in ONE or with purified XendoU. The processing product I-4 RNA was gel-purified and reverse transcribed (SS pre-amplification system—GIBCO) with the 5' terminally labeled oligonucleotide UHindIII (5'-AAGCT-TCTTCATGGCGGCTCGGCCAAT-3', SEQ ID NO: 9) complementary to 19 nucleotides at the 3' end of the downstream exon. The elongated products were run in parallel with the sequence obtained with the same primer on U86-containing precursor.

Results

Purification of XendoU from *X. laevis* Oocyte Nuclear Extracts

The authors previously developed an in vitro system able to reproduce the release of U16 snoRNA from its host intron (Caffarelli et al., 1994). When $^{32}$P-labelled U16-containing precursor is incubated in *X. laevis* oocyte nuclear extract, in the presence of $Mn^{++}$ ions, specific products, originating from endonucleolityc cleavages, are found (FIGS. 1A and 1B): the I-2 and I-1 molecules derive from cleavage upstream from U16 coding region, while I-3 and I-4 molecules are produced by cleavage downstream from U16. When double cleavage occurs on the same pre-mRNA molecule, pre-U16 products accumulate, which are then converted to the mature snoRNA by exonucleotidic digestion.

Figure 1B:
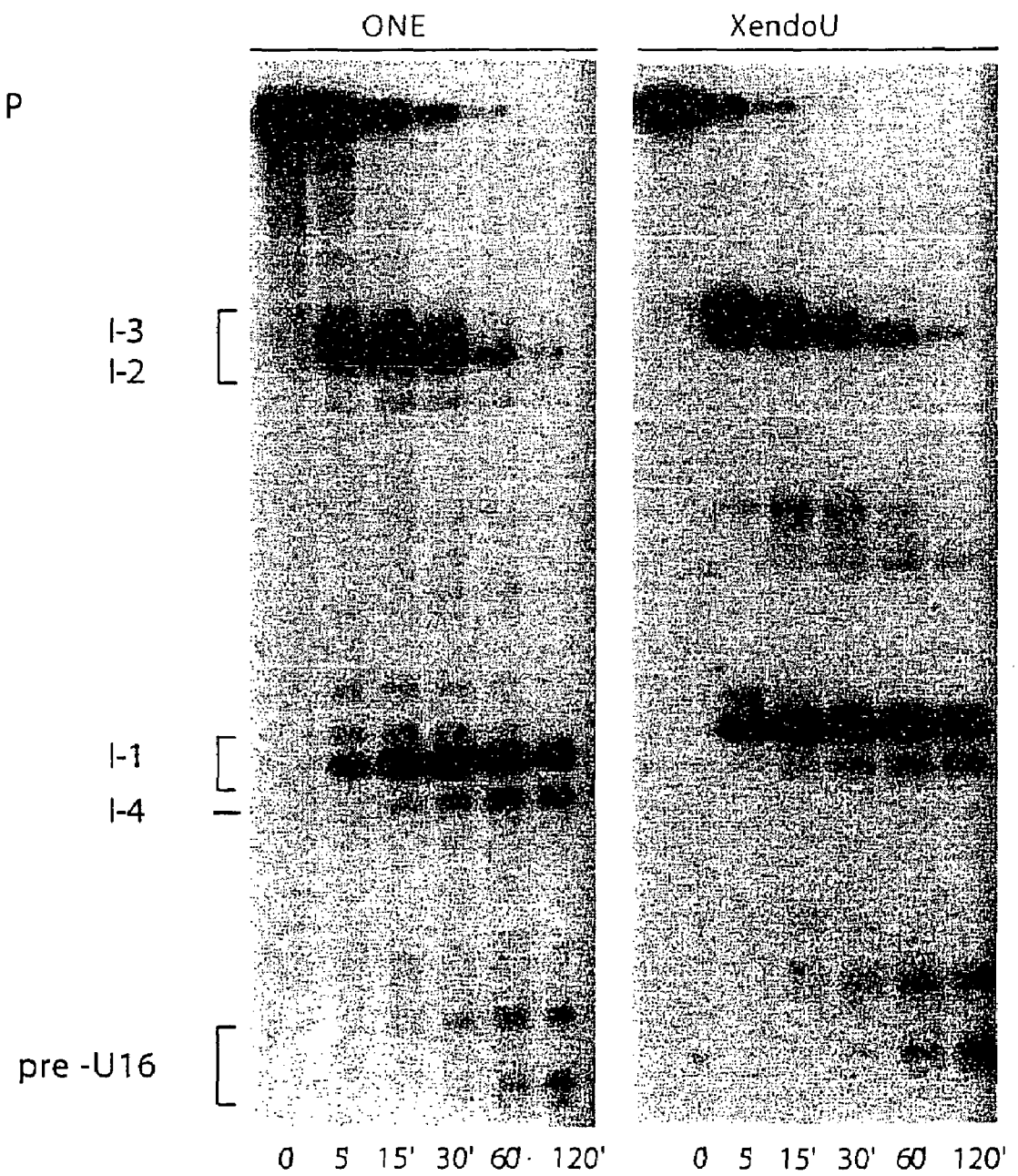
Figures 1C, 1D:
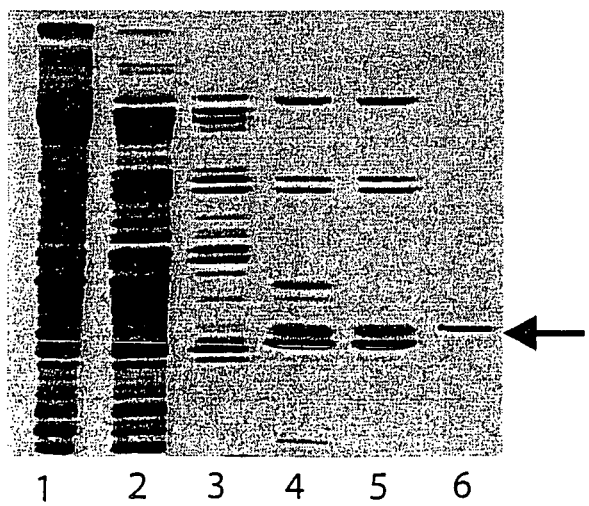

The procedure of biochemical characterization is indicated in FIG. 1C, while the protein content of the fractions displaying XendoU activity is shown in FIG. 1D. After several chromatographic steps, a single protein of 37 kDa molecular mass was obtained as showed in FIG. 1D, lane 6. The elution of XendoU activity during the last purification step on gel filtration column is consistent with a monomeric protein of 37 kDa. The assay for testing the presence of XendoU activity was performed by incubating $^{32}$P-labelled U16-containing precursor with aliquots of the different fractionation steps. FIG. 1B shows the comparison of XendoU activity of unfractionated nuclear extracts (ONE) with that of the gel filtration column (XendoU). Since previously it was demonstrated the dependence of XendoU activity on $Mn^{++}$ ions, this cofactor is always present in the reaction: in both cases the same primary cleavage products, I-2 and I-3 and their complementary molecules I-1 and I-4, are generated. Primer extension analysis performed on cleavage products I-2 and I-4 revealed that the purified enzyme cleaves intronic sequences at the same U-rich in vivo recognized areas (Caffarelli et al., 1994).

Characterization of XendoU Cleavage

Figure 2:
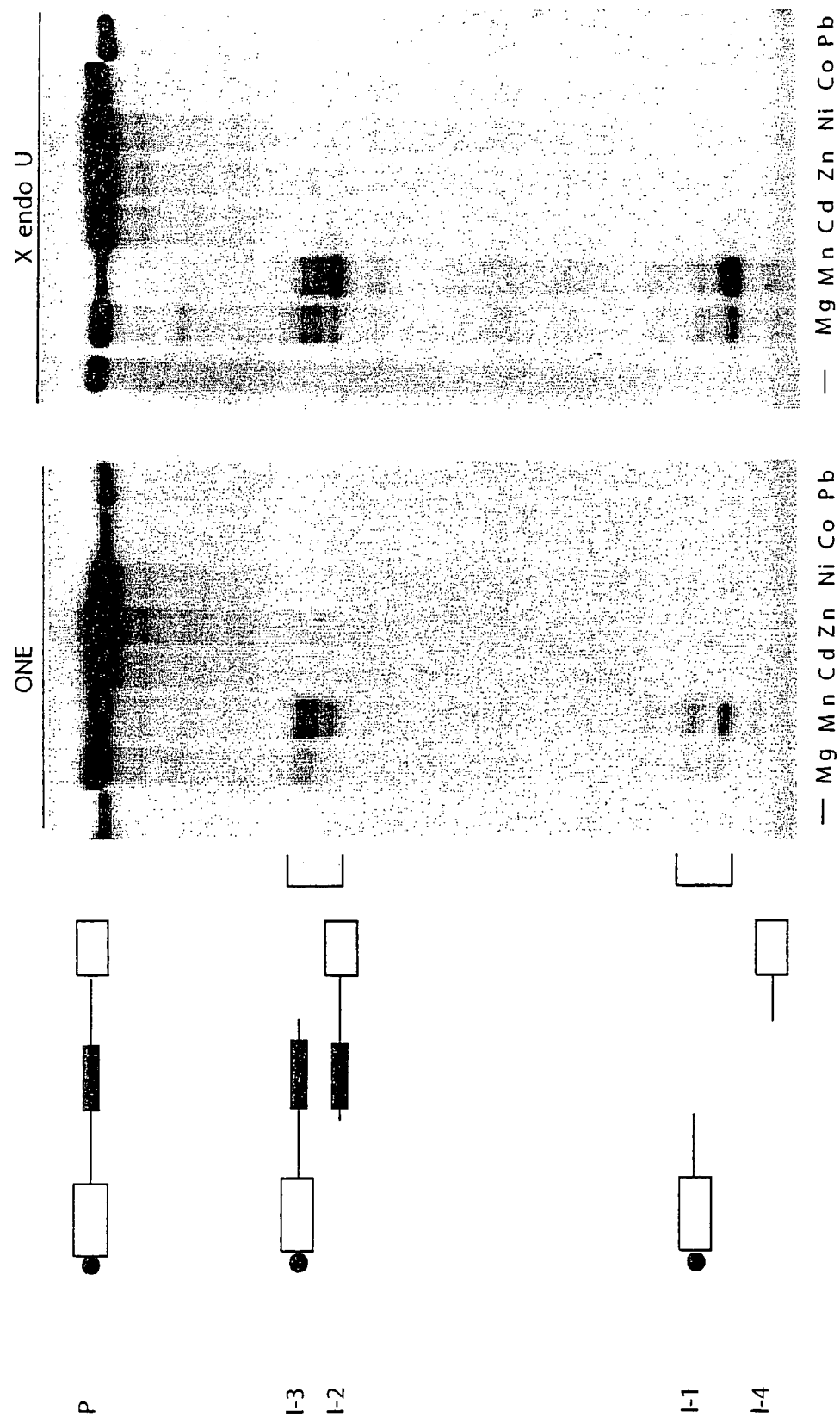
FIG. 2 shows XendoU cleavage which requires $Mn^{++}$ cations. $^{32}$P-labelled 003 RNA was incubated in oocyte nuclear extract (ONE) or with purified XendoU (XendoU, GeneBank TM/EBI Data Bank AJ507315) in the presence of different metal ions at a concentration of 6 mM. After 30 min, the reaction was stopped and the processing products analysed on 6% polyacrilamide-7M urea gel. In the lane—the RNA substrate was incubated with XendoU in the absence of ions. The specific cleavage products are schematised on the left side.

The analysis of the ion dependence of cleavage was carried out by incubating $^{32}$P-labelled U16 containing precursor with ONE or with purified XendoU in the presence of different cations as shown in FIG. 2. In both cases $Cd^{++}$, $Zn^{++}$, $Ni^{++}$, $Co^{++}$ and $Pb^{++}$ do not activate cleavage; whereas $Mn^{++}$, and to a minor extent $Mg^{++}$, produce the appearance of the specific cleavage products. These results indicate a $Mn^{++}$ ion requirement for XendoU full activity.

Figure 3A:
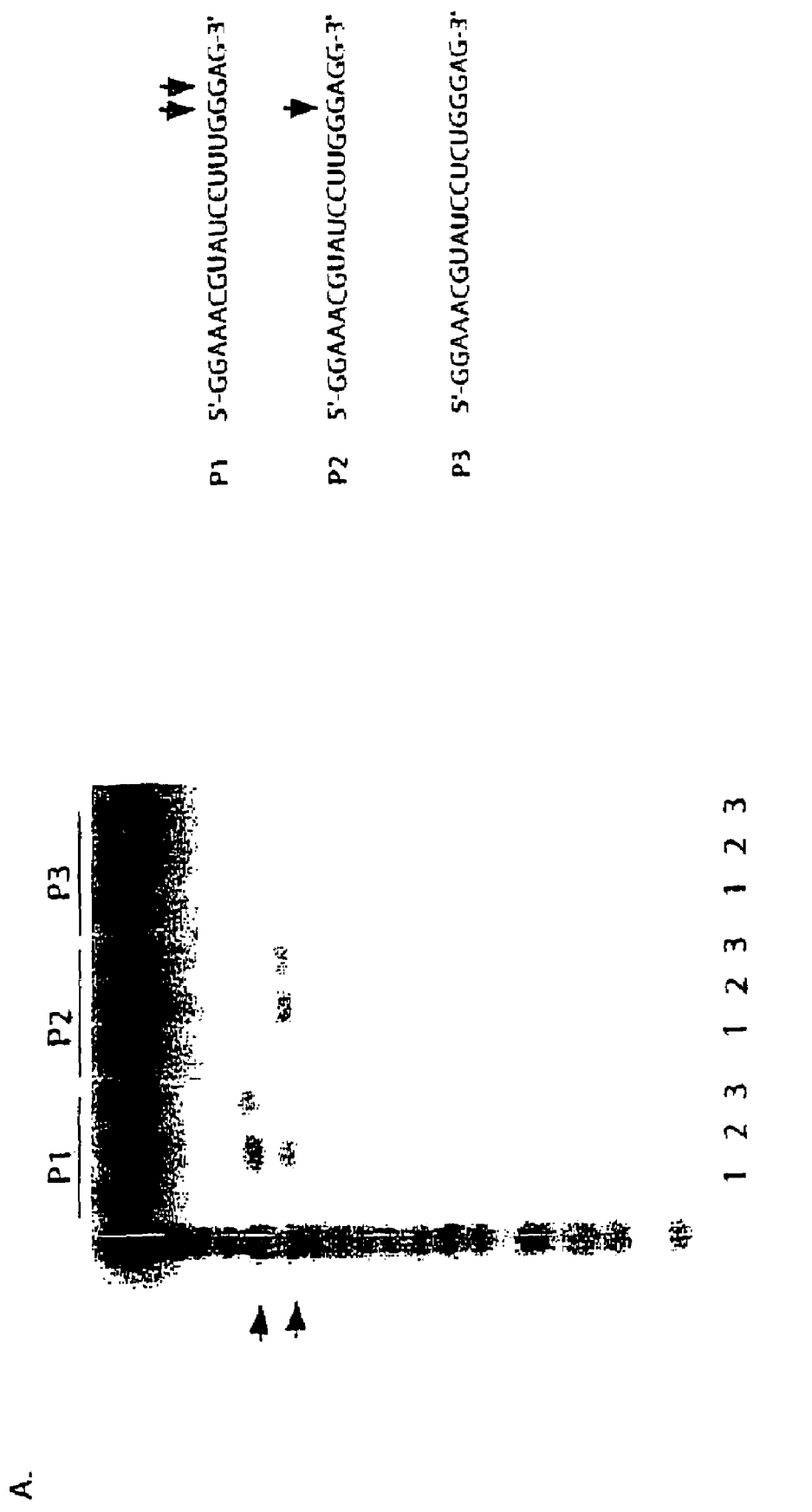
FIG. 3 shows that the XendoU activity is U-specific and produces 2'-3' cyclic phosphate. A, $^{32}$P ATP labelled synthetic oligoribonucleotide PI, SEQ ID NO: 3, containing the distal cleavage site upstream from U16, and its mutant derivatives (P2, SEQ ID NO: 4; P3, SEQ ID NO: 5) were incubated with the unfractionated extract (lanes 2) or with purified XendoU (lanes 3), under standard conditions for 30 min. RNA molecules were extracted and analysed on 10% polyacrylamide-7M urea gel. In lanes 1 untreated RNA is shown, in lane M-RNA marker generated by alkaline digestion of P1 (SEQ ID NO: 3) is shown; arrows indicate cleavage sites. On the right side the sequences of the oligoribonucleotides are reported. B, The $^{32}$P-labeled 1-1 molecules, schematically represented on the left side, generated by incubation of U16-containing precursor in ONE (ONE), with purified XendoU (XendoU) or after injection in oocytes (in vivo), were gel purified, and their 3'end analysed. The molecules were incubated with 1 unit of alkaline phosphatase (lane 1) or with 10 mM HCl (lanes 2) or with alkaline phosphatase after acid treatment (lanes 3). After incubation the RNAs extracts were analysed by electrophoresis on 10% polyacrylamide-7M urea gel. Untreated molecules were run as control in lanes 4.

The substrate selectivity of XendoU was further addressed by incubating the purified enzyme with synthetic oligoribonucleotide (P1, SEQ ID NO: 3), containing the distal XendoU cleavage site (site d, FIG. 1A), localised upstream from U16, and with mutated derivatives thereof (P2, SEQ ID NO: 4 and P3, SEQ ID NO: 5). The obtained results, shown in FIG. 3A, indicate that XendoU displays the same selectivity observed in vivo and that the minimal consensus cleavage site is an uracyl dimer.

The incubation of the enzyme with double stranded oligoribonucleotides, of 21 nucleotides, containing U-rich sequences demonstrated that only single stranded RNAs are recognized by XendoU.

Figure 3B:
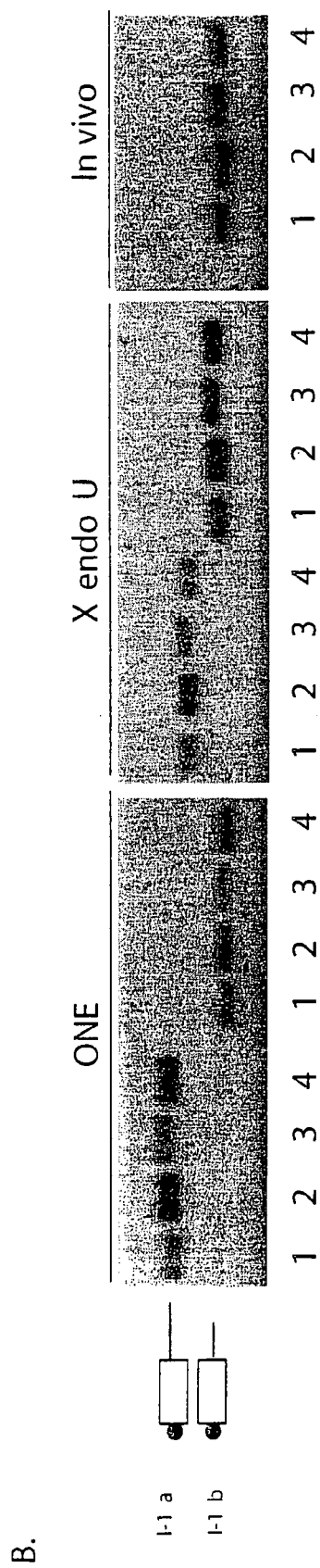

The chemistry of XendoU cleavage was then assessed by determining the chemical nature of the ends of the cleaved products; To this aim we analysed the ends of $^{32}$P-labelled I-1a and I-1b molecules produced with ONE or with the purified XendoU: these molecules were gel purified and treated with alkaline phosphatase, HCl, or both. FIG. 3B shows that a slight decrease in migration, due to the loss of a negative charge, is obtained when the alkaline phosphatase treatment follows the HCl treatment (lanes 3). This result is obtained both with ONE (lanes ONE) and purified XendoU (lanes XendoU) and indicates that the 3' end of the molecules bears a phosphate group which is present in a 2'-3' cyclic form (Lund and Dahiberg, 1992; Forster et al., 1990). In fact, only after the acidic treatment the phosphate group can be removed by phosphatase resulting in a slight electrophoresis delay. This effect is observed both for the I-1a and I-1b molecules obtained with unfractionated oocyte nuclear extract and with XendoU. As previously reported (Caffarelli et al., 1996), the products of primary cleavage such as I-1 molecules, are in vivo unstable being rapidly degraded, after cleavage. Nevertheless, after very short incubation times, little amounts of I-1b molecules can be purified and subjected to the same treatment as described above. FIG. 3B (lanes in vivo) indicates that also in this case a slight delay in migration is obtained (lane 3), demonstrating that the products of the in vivo reaction display 2'-3' cyclic phosphates as well.

Isolation of cDNA for XendoU

After purification, protein samples from SDS-PAGE were reduced, alkylated and digested with trypsin as reported in the experimental section. The resulting peptide mixture was resolved by R-HPLC and selected peptide fractions were submitted to automated Edman degradation. The three sequence portions determined are reported in FIG. 4 (indicated as 1, 2 and 3). From these amino acid sequences, degenerated oligonucleotides were derived and employed in different combinations and different orientation in PCR amplification reactions on cDNA from polyA$^+$ RNA extracted from *X. laevis* oocytes. Only the reaction performed with sequence 1 (forward) and sequence 3 (reverse) resulted in an amplification product (500 bp). Sequencing of this product indicated the presence of an Open Reading Frame containing peptide 2. This cDNA probe was then utilised for the screening of a *X. laevis* stage 28 embryo cDNA library, allowing the isolation of a full-length cDNA (SEQ ID NO: 1). The amino acid sequence determined was confirmed by MALDI-MS spectra of the tryptic peptides. In fact, signals observed at m/z 565.29, 814.45, 1004.48, 10025.54, 1132.59, 1190.60, 1490.78, 1504.80, 1520.70, 1729.91, 1758.82, 1988.08, 2000.00, 2014.01, 2076.99, 2162.98, 2234.14, 2238.05, 2394.15, 2432.26, 3058.51 and 3370.66 were ascribed to peptides 196-200, 126-132, 117-124, 6-14, 117-125, 41-52, 114-125, 260-271, 15-26, 137-149, 53-67, 256-271, 53-69, 275-292, 204-220, 150-169, 133-149, 171-188, 170-188, 117-136, 6-31 and Ac4-31. This result allowed to cover 65% of the entire sequence, explaining the reluctance of a blotted protein sample to Edman degradation.

Cloning and Expression of XendoU cDNA

Figure 5A:
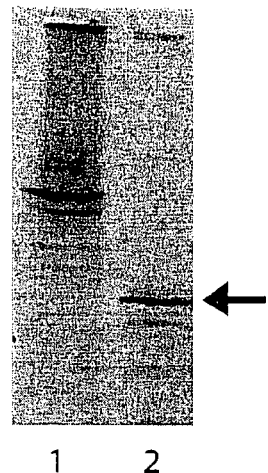
FIG. 5 shows the functional analysis of in vitro translated XendoU A, SDS-PAGE analysis of [$^{35}$S] Methionine-labelled XendoU (lane 2) and of control luciferase (lane 1) produced by in vitro transcription and translation. The arrow points to XendoU protein. B, 003 RNA was incubated, in the presence of $Mn^{++}$ ions, in ONE (ONE), with XendoU produced by reticulocyte lysate (ret-XendoU/+Mn), or with reticulocyte lysate as such (lane ret/+Mn). As control 003 RNA was incubated, in the absence of $Mn^{++}$ ions, with XendoU produced by reticulocyte lysate (lanes ret-XendoU/−Mn). The numbers below indicate incubation times: 0 min (lane 1), 45 min (lanes 2).
Figure 5B:
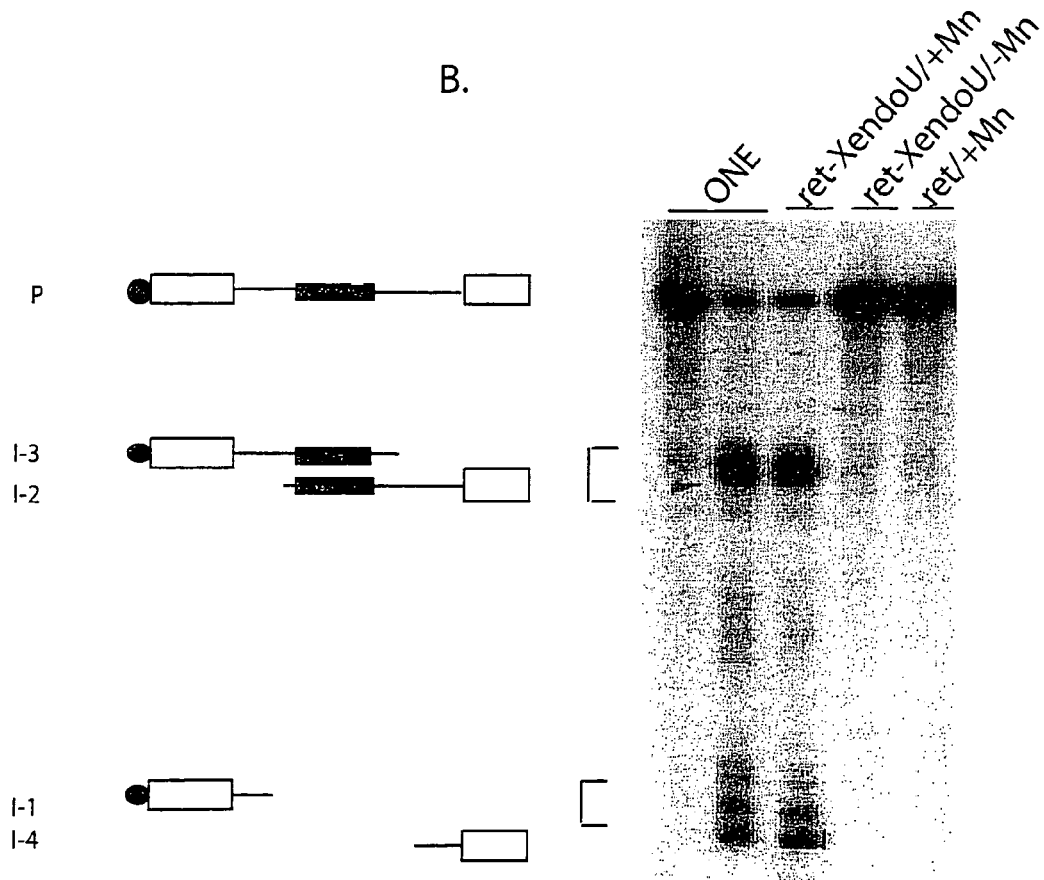

XendoU ORF, 876 bp, was cloned into Blue Script vector and the protein was produced by in vitro transcription and translation using reticulocyte lysate. The translational product was analysed on SDS-PAGE revealing a protein of 37 kDa molecular mass (FIG. 5A). In order to assess the nature of the 37 kDa protein, enzymatic activity was assayed by incubating the $^{32}$P-labelled RNA substrate in reticulocyte lysate expressing XendoU ORF. The activity assay was carried out in parallel with the unfractionated extract: FIG. 5B shows that the cleavage products generated by the translated 37 kDa protein (lane ret-XendoU/+Mn) exactly match those obtained with the extract (lanes ONE). Furthermore, the lack of cleavage when $Mn^{++}$ ions are not added to the reaction mixture (lane ret-XendoU/−Mn) confirms the specific ion requirement for XendoU and suggests that the binding to the cofactor is reversible. As negative control the activity assay was carried out by incubating RNA substrate in reticulocyte lysate as such in the presence of $Mn^{++}$ ions (lane ret/+Mn).

XendoU also Participates to U86 snoRNA Biosynthesis

Figure 6A:
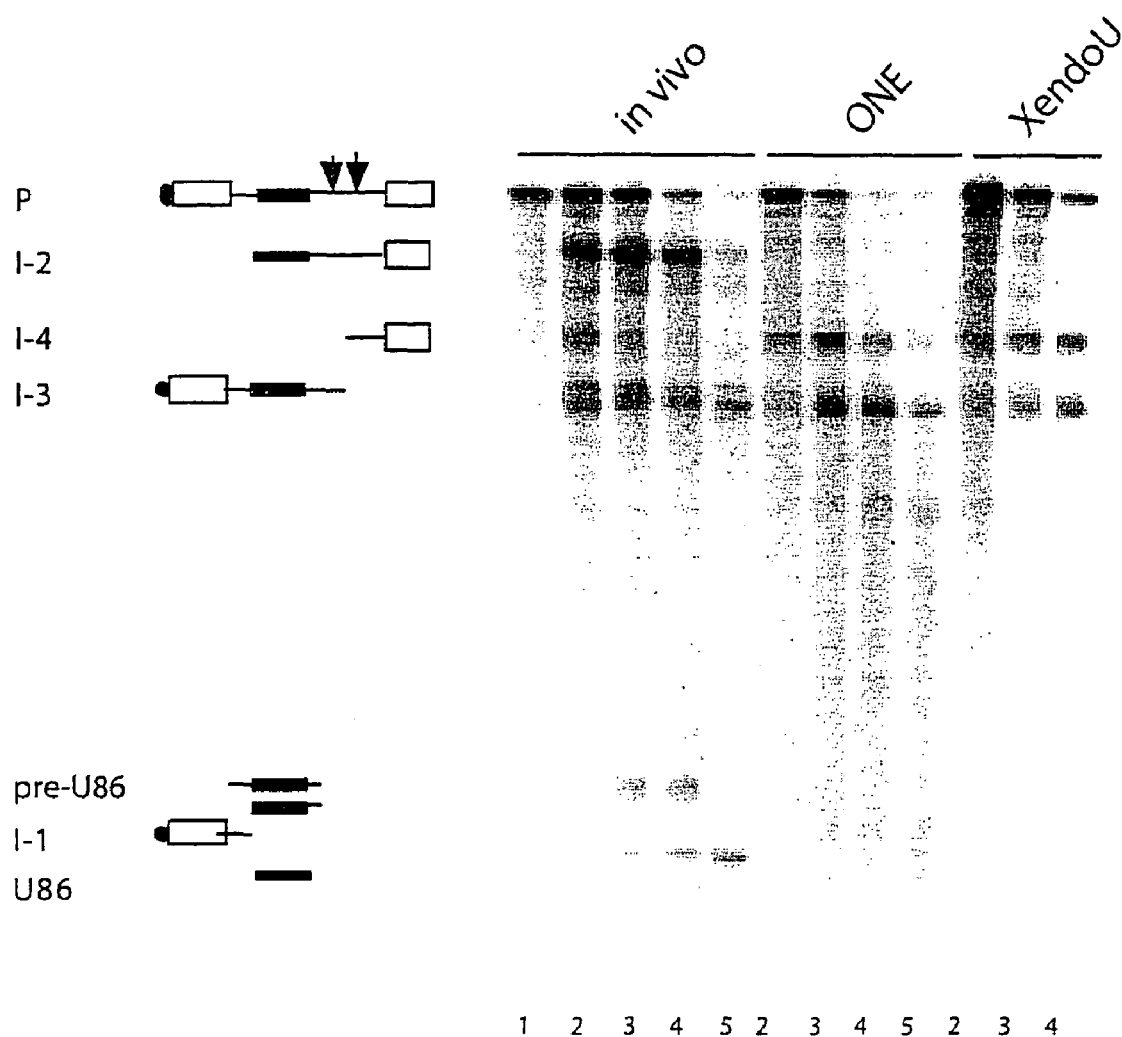
FIG. 6 shows that XendoU is involved in U86 snoRNA biosynthesis. A, U86 processing is analysed in vivo by injection of $^{32}$P-labelled U86-containing precursor (P) in *X. laevis* oocytes (lanes in vivo), or in vitro by incubation of the RNA precursor in ONE (ONE), or with purified XendoU (XendoU). The numbers below indicate different incubation times: 0 min (lane 1), 10 min (lanes 2), 45 min (lanes 3), 3 hours (lanes 4), 16 hours (lanes 5). RNA was then extracted and loaded on a 6% polyacrilamide-7M urea gel. The processing products are schematised aside. Arrows indicate specific XendoU cleavages. B, $^{32}$P-labelled UhindIII primer, depicted below, was reacted with unlabelled 1-4 molecules obtained after 10 min of incubation in oocytes (lane in vivo), 45 min of incubation in ONE (ONE) or 45 min of incubation with purified XendoU (XendoU). The products of primer extension were run in parallel with the sequence (lane G, A, T, and C) performed with the same oligonucleotide on U86. The sequence is reported on the left side (SEQ ID NO: 10): the arrow points to the XendoU cleavage sites. C, U86-containing precursor was incubated, in the presence of $Mn^{++}$ ions, in ONE (ONE), with XendoU produced by reticulocyte lysate (ret-XendoU/+Mn), or with reticulocyte lysate as such (lanes ret/+Mn). As control, pre-mRNA was incubated with XendoU produced by reticulocyte lysate in the absence of $Mn^{++}$ ions (ret-XendoU/−Mn\ The numbers below indicate incubation times: 0 min (lane 1), 45 min (lanes 2).

The authors previously identified a snoRNA, named U86, encoded by an intron of Nop56 gene of *X. laevis*. It was also shown that U86 has homologs both in human, where it displays the same genomic organization, and in yeast where it is embedded in the ORF of Rib1 gene (Filippini et al., 2001). As U16 snoRNA, also U86 is contained in a very poorly spliceable intron and its biosynthesis appears to be alternative to that of the co-transcribed mRNA. The injection of $^{32}$P-labelled U86-containing precursor into *X. laevis* oocytes generates the truncated products I-2 and I-3 and their 5' and 3' complementary molecules, 1-1 and 1-4, by means of upstream and downstream cleavages from U86 coding region (FIG. 6A, lanes in vivo).

Figure 6B:
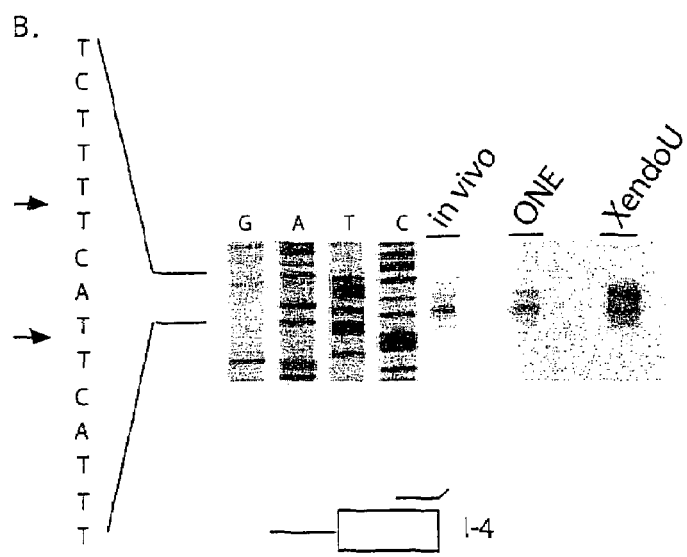
Figure 6C:
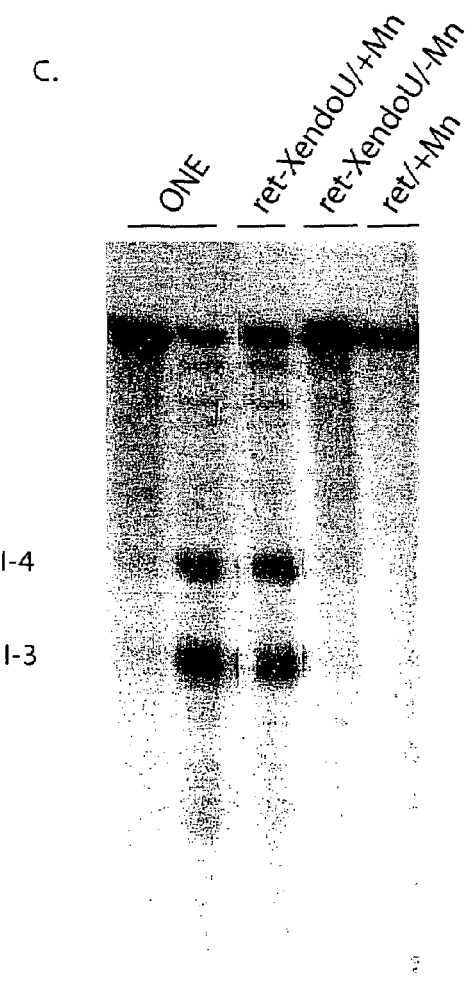

Processing of U86-containing precursor with purified XendoU (FIG. 6A, lanes XendoU) or with the reticulocyte lysate expressing XendoU ORF (FIG. 6C, lane ret-XendoU/+Mn) demonstrates that the enzyme is responsible for the occurring cleavage downstream from U86 coding region. The effector of the cleavage upstream from U86, that produces I-2 and I-1 molecules, is not yet known and it is lost in oocyte nuclear extracts (FIG. 6A, lanes ONE). The XendoU cleavage sites, downstream from U86, were determined by primer extension on 1-4 molecules and correspond to two U-rich sequences (FIG. 6B).

BIBLIOGRAPHY

Allmang, C., KufEL, J., Chanfreau, G., Mitchell, P., Petfaiski E. and Tollervey, D. (1999) Functions of the exosome m rRNA, snoRNA and snRNA synthesis. EMBO J. 18, 5399-5410.

Ambros. V. (2001) Dicing up RNAs. Science 293, 811-813

Bachellerie, J. P., Cavaille, J. and Qu, L. H. (2000) Nucleotide modifications of eukaryotic rRNAs: the worid of small nucleolar RNA guides revisited. The Ribosome: structure, function, antibiotics, and cellular interactions. (2000 ASM Press, Washington, D.C.) pp. 191-203.

Bachmann, M., Messer, R., Trautmann, F. and Muller, W. E. G. (1984) 12S small nuclear ribonucleoprotein-associated acidic and pyrimidine-specific endoribonuclease from calf thymus and L5178y cells. Biochim. Biophys. Acta 783, 89-99.

Bernstein, E., Caudy, A. A., Hammond, S. M. and Hannon, G. J. (2001) Role for a bidentate ribonuclease in the intiation step of RNA interference. Nature 409, 363-366.

Bujnicki, J. M., and Rychlewski, L. (2000) Prediction of a common fold for all four subunits of the yeast tRNA splicing endonuclease: implications for the evolution of the EndA/Sen family. FEBS Lett. 486, 328-9.

Caffarelli, E., Losito, M., Giorgi, C., Fatica, A., and Bozzoni, I; (1998) in vivo identification of nuclear factors interacting with the conserved elements of box C/D small nucleolar RNAs. Mol. Cell. Biol. 2, 1023-1028.

Caffarelli, E., Arese, M., Santoro, B., Fragapane, P., and Bozzoni, I. (1994) Invitro study of processing of the intron-encoded U16 small nucleolar RNA in *Xenopus laevis*. Mol. Cell. Biol. 14, 2966-2974

Caffarelli, E., Fatica, A., Prislei, S., De Gregorio, E., Fragapane, P., and Bozzoni, I. (1996) Processing of the intron-encoded U16 and U18 snoRNAs: the conserved c and D boxes control both the processing reactions and the stability of the mature snoRNA. EMBO J. 5, 1121-1131.

Castano, J. G., Tobian, J. A., and Zasloff, M. (1985) Purification and characterization of an endonuclease from *Xenopus laevis* ovaries which accurately processes the 3' terminus of human pre-tRNA-Met(i) (3' pre-tRNase). J. Biol. Chem. 260, 9002-9008

Chanfreau. G., Elela, S. A., Ares, M. Jr., and Guthrie, C. (1997) Alternative 3'-end processing of U5 snRNA by RNase III. Genes Dev. 11, 2741-2751

Chanfreau, G., Legrain, P., and Jacquier, A. (1998) Yeast RNase III as a key processing enzyme in small nucleolar RNAs metabolism. J. Mol. Biol. 284, 975-88.

Cirino, N. M., Cameron, C. E., Smith, J. S., Rausch, J. W., Roth, M. J., Benkovic, S. J. and Le Grice, S. F. (1995) Divalent cation modulation of the ribonuclease functions of human immunodeficiency virus reverse transcriptase. Biochemistry 34, 9936-9943.

Court, D. (1993) Rnase III: a double-strand processing enzyme. In: Brawerman, G. and Belasco, J, eds Control of mRNA stability. (New York, Academic, Press), pp. 70-116.

Dange, V., Van Atta, R. B. and Hecht, S. M. (1990) A $Mn2(+)$-dependent ribozyme. Science 248, 585-588.

Deutscher, M. P. (1985) *E. coli* RNAses: making sense of alphabet soup. Cell 40, 731-732.

Deutscher, M. P. (1993) Ribonuclease multiplicity, diversity, and complexity, J. Biol. Chem. 268, 13011-13014

Eder, P. S. and Walder, J. A. (1991) Ribonuclease H from K562 human erythroleukemia cells. Purification, characterization, and substrate specificity. J. Biol. Chem. 266, 6472-6479, Elela, S. A., Igel, H., and Ares. M. Jr. (1996) Rnase III cleaves eukaryotic preribosomal RNA at a U3 snoRNP-dependent site. Cell, 85, 115-124.

Filippini, D., Renzi, F., Bozzoni, I., and Caffarelli. E. (2001) U86, a novel snoRNA with an unprecedented gene organisation in yeast. Biochem. Biophys. Res. Commun. 288, 16-21

Forster, A. C., Davies, C., Hutchins, C. J. and Symons R. H. (1990) Characterization of self-cleavage of viroid and virusoid RNAs. Methods Enzymol. 181, 583-607

Fragapane, P., Prislei, S., Michienzi, A., Caffarelli, E. and Bozzoni I. (1993) A novel small nucleolar RNA (U16) is encoded inside a ribosomal protein intron and originates by processing of the pre-mRNA. EMBO J. 12, 2921-2928.

Freemont, P. S., Friedman, J. M., Beese, L. S., Sanderson M. R. and Steitz, T. A. (1988) Cocrystal structure of an editing complex of Klenow fragment with DNA Proc. Natl. Acad. Sci. USA 85, 8924-8928.

Gandini-Attardi, D., Margarit, I. and Tocchini-Valentini, G. P. (1985) Structural alteration in mutant precursors of the yeast $tRNA_3^{Leu}$ gene which behave as detective substrates for a highly purified splicing endoribonuclease. EMBO J. 4, 3289-3297.

Gandini-Attardi, D., Baldi, I. M., Mattoccia, E., and Tocchini-Valentini G. P. (1990) Transfer RNA splicing endonuclease from *Xenopus laevis*. Methods Enzymol. 181, 510-517.

Giorgi, C., Fatica, A., Nagel, R., and Bozzoni, I. (2001) Release of U18 snoRNA from its host intron requires interaction of Nop1p with the Rnt1p endonuclease. EMBO J. 20, 6856-65.

Hirose, T., and Steitz J. A. (2001) Position within the host intron is critical for efficient processing of box C/D snoRNAs in mammalian cells. Proc. Natl. Acad. Sci. USA 98, 12914-12919.

Kazakov, S. and Altman, S. (1992) A trinucleotide can promote metal ion-dependent specific cleavage of RNA. Proc. Natl. Acad. Sci. USA 89, 7939-7943.

Kufel, J., Dichtl, B., and Tollervey, D. (1999) Yeast Rntip is required for cleavage of the pre-ribosomal RNA in the 3' ETS but not the 5' ETS. RNA 5, 909-917

Lygerou. Z., Allmang, C., Tollervey, D., and Seraphin, B. (1996) Accurate processing of a eukaryotic precursor ribosomal RNA by ribonuclease MRP in vitro. Science 272, 268-270

Lund, E. and Dahlberg J. E. (1992) Cyclic 2',3'-phosphates and nontemplated nucleotides at the 3'end of spliceosomal U6 small nuclear RNA's. Science 255, 327-330

Maxwell, E. S. and Fournier, M. J. (1995) The small nucleolar RNAs. Annu. Rev. Biochem. 64, 897-934

McDowall, K. J., Kaberdin, V. R., Wu, S. W., Cohen, S. N. and Lin-Chao, S. (1995) Site specific RNase E cleavage of oligonucleotides and inhibition by stem-loops. Nature 374, 287-290

Nashimoto, M., (1995) Conversion of mammalian tRNA 3' proessing endoribonuclease to four-base-recognising RNA cutters. Nucl. Acids Res. 23, 3642-3647

Nicholson, A. W. (1997) in Ribonucleases: structures and functions, eds. D'Alessio, G. and Riordan, J. F. (Academic New York), pp. 1-49

Pan, T., Long, D. M. and Uhlenbeck. O. C. (1993) The RNA World, ed. R. F. Gesteland and J. F. Atkins, CSHL Press, 271-302.

Peebies, C. L., Gegenheimer, P., and Abelson, J. (1983) Precise excision of intervening sequences from precursor tRNAs by a membrane-associated yeast endonuclease. Cell 32, 525-536.

Prislei, S., Sperandio, S., Fragapane, P., Caffarelli, E., Presutti, C. and Bozzoni, I. (1992) The mechanisms controlling ribosomal protein L1 pre-mRNA splicing are maintained in evolution and rely on conserved intron sequences. Nucl. Acids Res. 17, 4473-4479

Prislei, S., Fatica, A., De Gregorio, E., Arese, M., Fragapane, P., Caffarelli, E., Presutti, C. and Bozzoni, I. (1995) Self-cleaving motifs are found in close proximity to the sites utilised for U16 snoRNA processing. Gene 163, 221-226.

Rauhut, R., Green, P. R., and Abelson, J. (1990). Yeast tRNA-splicing endonuclease is a heterotrimeric enzyme. J. Biol. Chem. 265, 18180-18184.

Schoenberg, D. R., and Chemokaiskaya, E. (1997) Ribonucleases involved in eukaryotic mRNA turnover, p. 217-240. In J. Harford and D. R. Morris (ed.), mRNA metabolism and post-transcriptional gene regulation. Wiley, New York; N.Y.

Steitz, J. A. and Steitz, T. A. (1993) A general two-metal-ion mechanism for catalytic RNA. Proc. Natl. Acad. Sci. USA 90, 6498-6502.

Trotta, C. R., Miao, F., Am, E. A., Stevens, S. W., Ho, C. K., Rauhut, R., and Abelson, J. N. (1997) The yeast tRNA splicing endonuclease: a tetrameric enzyme with two active site subunits homologous to the archaeal tRNA endonucleases. Cell 89, 849-58

Zamore P. D. (2001) Thirty-three years later, a glimpse at the ribonuclease III active site. Molecular Celi 8, 1158-1160

Watkins, N. J., Segault, V., Charpentier, B., Nottrott, S., Fabrizio, P., Bachi, A., Wilm, M., Rosbash, M., Branlant, C., and Luhrmann, R. (2000) A common core RNP structure shared between the small nucleolar box CID RNPs and the spliceosomal U4 snRNP. Cell 103, 457-466.

The invention claimed is:

1. An isolated nucleic acid comprising SEQ ID No 1.

2. A recombinant vector able to express the nucleic acid according to claim 1 in prokaryotes.

3. A recombinant vector able to express the nucleic acid according to claim 1 in eukaryotes.

4. An isolated nucleic acid sequence consisting of SEQ ID No 1.

* * * * *

SEQUENCE LISTING

```
<160> NUMBER OF SEQ ID NOS: 9

<210> SEQ ID NO 1
<211> LENGTH: 1265
<212> TYPE: DNA
<213> ORGANISM: Xenopus laevis
<220> FEATURE:
<221> NAME/KEY: misc_feature
<222> LOCATION: (1)..(38)
<223> OTHER INFORMATION: 5 untranslated DNA region
<220> FEATURE:
<221> NAME/KEY: exon
<222> LOCATION: (39)..(915)
<220> FEATURE:
<221> NAME/KEY: terminator
<222> LOCATION: (916)..(918)
<220> FEATURE:
<221> NAME/KEY: misc_feature
<222> LOCATION: (916)..(1265)
<223> OTHER INFORMATION: 3 untranslated DNA region

<400> SEQUENCE: 1
attggggaac tgggagcaga gagtgacggg caggagcc atg gcg agt aac agg ggg        56
                                         Met Ala Ser Asn Arg Gly
                                           1               5 cag ctg aac cat gaa ctc tcc aag ctg ttt aat gag ctg tgg gac gca        104
Gln Leu Asn His Glu Leu Ser Lys Leu Phe Asn Glu Leu Trp Asp Ala
         10                  15                  20 gat cag aac cgg atg aag tcc ggg aag gat tat cgg atc tcc ttg cag        152
Asp Gln Asn Arg Met Lys Ser Gly Lys Asp Tyr Arg Ile Ser Leu Gln
     25                  30                  35 ggt aaa gca ggg tac gta ccc gcc ggt tcc aac cag gcc agg gac agc        200
```

|   |   |   |   |   |   |   |   |   |   |   |   |   |   |
|---|---|---|---|---|---|---|---|---|---|---|---|---|---|
| Gly | Lys | Ala | Gly | Tyr | Val | Pro | Ala | Gly | Ser | Asn | Gln | Ala | Arg | Asp | Ser |
|  | 40 |  |  |  | 45 |  |  |  | 50 |  |  |  |  |

```
gcc tcg ttc ccg ctc ttc cag ttc gtc gat gag gag aag ctg aag agc    248
Ala Ser Phe Pro Leu Phe Gln Phe Val Asp Glu Glu Lys Leu Lys Ser
 55              60                  65                  70 agg aag acg ttt gca acc ttc att tcc ctg ctg gac aat tat gag atg    296
Arg Lys Thr Phe Ala Thr Phe Ile Ser Leu Leu Asp Asn Tyr Glu Met
                 75                  80                  85 gac acg ggg gtg gcc gag gtt gtg act ccg gag gaa atc gct gaa aac    344
Asp Thr Gly Val Ala Glu Val Val Thr Pro Glu Glu Ile Ala Glu Asn
             90                  95                 100 aac aac ttc ctg gac gcc att ctg gaa acc aaa gtg atg aag atg gca    392
Asn Asn Phe Leu Asp Ala Ile Leu Glu Thr Lys Val Met Lys Met Ala
            105                 110                 115 cat gac tac ctg gtg agg aag aac caa gcc aaa ccc acc cgg aat gac    440
His Asp Tyr Leu Val Arg Lys Asn Gln Ala Lys Pro Thr Arg Asn Asp
        120                 125                 130 ttc aag gtc caa ctg tac aac atc tgg ttc cag ctg tac tca cgg gcc    488
Phe Lys Val Gln Leu Tyr Asn Ile Trp Phe Gln Leu Tyr Ser Arg Ala
135                 140                 145                 150 cca ggg agc aga ccc gat tcg tgc ggc ttt gag cac gtg ttt gtg gga    536
Pro Gly Ser Arg Pro Asp Ser Cys Gly Phe Glu His Val Phe Val Gly
                155                 160                 165 gaa tcg aag cga ggg cag gag atg atg ggg ctt cac aac tgg gtc cag    584
Glu Ser Lys Arg Gly Gln Glu Met Met Gly Leu His Asn Trp Val Gln
            170                 175                 180 ttt tac ctt cag gag aag agg aag aac atc gac tat aaa gga tac gtg    632
Phe Tyr Leu Gln Glu Lys Arg Lys Asn Ile Asp Tyr Lys Gly Tyr Val
        185                 190                 195 gct cgg cag aac aag agt cgg ccg gat gaa gat gat cag gtg ttg aac    680
Ala Arg Gln Asn Lys Ser Arg Pro Asp Glu Asp Asp Gln Val Leu Asn
    200                 205                 210 ctg cag ttc aat tgg aag gag atg gtg aaa ccc gtc ggc agc agc ttc    728
Leu Gln Phe Asn Trp Lys Glu Met Val Lys Pro Val Gly Ser Ser Phe
215                 220                 225                 230 att ggc gtc agc ccg gaa ttc gaa ttc gcc ctt tac acc atc gtc ttc    776
Ile Gly Val Ser Pro Glu Phe Glu Phe Ala Leu Tyr Thr Ile Val Phe
                235                 240                 245 ctc gcg tct cag gag aag atg agc cga gaa gtc gtt cgg ctg gaa gaa    824
Leu Ala Ser Gln Glu Lys Met Ser Arg Glu Val Val Arg Leu Glu Glu
            250                 255                 260 tac gaa ctg cag atc gtc gtc aat cgc cac ggc cgt tat ata ggg acc    872
Tyr Glu Leu Gln Ile Val Val Asn Arg His Gly Arg Tyr Ile Gly Thr
        265                 270                 275 gcc tac ccc gtc ctc ctg agc acc aat aac ccg gat ctg tac t          915
Ala Tyr Pro Val Leu Leu Ser Thr Asn Asn Pro Asp Leu Tyr
    280                 285                 290 gaggggcgg ggctagagat cacagccggt tcccacggtt tgggtgcatt tactaacaaa    975
actgcaccaa tgcaacaatg caagcagata atgggggcag gtccatatcc ctctgctttc   1035
cctagcgtgt gtggggcaca ttaacccctat aactgtcact cactgcacca gacccattat  1095
ttaaccccac aagggacatc aagccagtgc cttgttatga gagagcgcag ccggggcttc   1155
tctactgtga aacttctgta ttgtatagag tttacttggt ttcttcctcc agacaatttc   1215 acttttttt tgctttgcct ttaaccatta aaagtccatg acatttctgt              1265

<210> SEQ ID NO 2
<211> LENGTH: 292
<212> TYPE: PRT
```

<213> ORGANISM: Xenopus laevis

<400> SEQUENCE: 2

```
Met Ala Ser Asn Arg Gly Gln Leu Asn His Glu Leu Ser Lys Leu Phe
1               5                   10                  15
Asn Glu Leu Trp Asp Ala Asp Gln Asn Arg Met Lys Ser Gly Lys Asp
            20                  25                  30
Tyr Arg Ile Ser Leu Gln Gly Lys Ala Gly Tyr Val Pro Ala Gly Ser
        35                  40                  45
Asn Gln Ala Arg Asp Ser Ala Ser Phe Pro Leu Phe Gln Phe Val Asp
    50                  55                  60
Glu Glu Lys Leu Lys Ser Arg Lys Thr Phe Ala Thr Phe Ile Ser Leu
65                  70                  75                  80
Leu Asp Asn Tyr Glu Met Asp Thr Gly Val Ala Glu Val Val Thr Pro
                85                  90                  95
Glu Glu Ile Ala Glu Asn Asn Phe Leu Asp Ala Ile Leu Glu Thr
            100                 105                 110
Lys Val Met Lys Met Ala His Asp Tyr Leu Val Arg Lys Asn Gln Ala
        115                 120                 125
Lys Pro Thr Arg Asn Asp Phe Lys Val Gln Leu Tyr Asn Ile Trp Phe
    130                 135                 140
Gln Leu Tyr Ser Arg Ala Pro Gly Ser Arg Pro Asp Ser Cys Gly Phe
145                 150                 155                 160
Arg His Val Phe Val Gly Glu Ser Lys Arg Gly Gln Glu Met Met Gly
                165                 170                 175
Leu His Asn Trp Val Gln Phe Tyr Leu Gln Glu Lys Arg Lys Asn Ile
            180                 185                 190
Asp Tyr Lys Gly Tyr Val Ala Arg Gln Asn Lys Ser Arg Pro Asp Glu
        195                 200                 205
Asp Asp Gln Val Leu Asn Leu Gln Phe Asn Trp Lys Glu Met Val Lys
    210                 215                 220
Pro Val Gly Ser Ser Phe Ile Gly Val Ser Pro Glu Phe Glu Phe Ala
225                 230                 235                 240
Leu Tyr Thr Ile Val Phe Leu Ala Ser Gln Glu Lys Met Ser Arg Glu
                245                 250                 255
Val Val Arg Leu Glu Glu Tyr Glu Leu Gln Ile Val Val Asn Arg His
            260                 265                 270
Gly Arg Tyr Ile Gly Thr Ala Tyr Pro Val Leu Leu Ser Thr Asn Asn
        275                 280                 285
Pro Asp Leu Tyr
    290
```

<210> SEQ ID NO 3
<211> LENGTH: 20
<212> TYPE: RNA
<213> ORGANISM: Artificial Sequence
<220> FEATURE:
<223> OTHER INFORMATION: Synthetic oligoribonucleotide
<220> FEATURE:
<221> NAME/KEY: misc_RNA
<222> LOCATION: (1)..(20)
<223> OTHER INFORMATION: Synthetic oligoribonucleotide which includes
      U16 upstream cleavage site

<400> SEQUENCE: 3
ggaaacguau ccuuugggag                                                   20

```
<210> SEQ ID NO 4
<211> LENGTH: 20
<212> TYPE: DNA
<213> ORGANISM: Artificial Sequence
<220> FEATURE:
<223> OTHER INFORMATION: Shyntetic oligonucleotide
<220> FEATURE:
<221> NAME/KEY: misc_RNA
<222> LOCATION: (1)..(20)
<223> OTHER INFORMATION: Mutant of SEQ ID 3
<220> FEATURE:
<221> NAME/KEY: variation
<222> LOCATION: (20)..(20)
<223> OTHER INFORMATION: "U" is replaced by "T"

<400> SEQUENCE: 4
ggaaacguau ccugggagt                                         20

<210> SEQ ID NO 5
<211> LENGTH: 20
<212> TYPE: RNA
<213> ORGANISM: Artificial Sequence
<220> FEATURE:
<223> OTHER INFORMATION: Synthetic oligoribonucleotide
<220> FEATURE:
<221> NAME/KEY: misc_RNA
<222> LOCATION: (1)..(20)
<223> OTHER INFORMATION: Mutant of SEQ ID 3
<220> FEATURE:
<221> NAME/KEY: variation
<222> LOCATION: (14)..(14)
<223> OTHER INFORMATION: "U" is replaced by "C"

<400> SEQUENCE: 5
ggaaacguau ccucugggag                                        20

<210> SEQ ID NO 6
<211> LENGTH: 20
<212> TYPE: RNA
<213> ORGANISM: Artificial Sequence
<220> FEATURE:
<223> OTHER INFORMATION: Synthetic oligoribonucleotide
<220> FEATURE:
<221> NAME/KEY: misc_RNA
<222> LOCATION: (1)..(20)
<223> OTHER INFORMATION: Mutant of SEQ ID 3
<220> FEATURE:
<221> NAME/KEY: variation
<222> LOCATION: (14)..(14)
<223> OTHER INFORMATION: "U" is replaced by "G"

<400> SEQUENCE: 6
ggaaacguau ccugugggag                                        20

<210> SEQ ID NO 7
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(27)
<223> OTHER INFORMATION: Primer

<400> SEQUENCE: 7
aagcttcttc atggcggctc ggccaat                                27

<210> SEQ ID NO 8
<211> LENGTH: 20
<212> TYPE: DNA
```

```
<213> ORGANISM: Artificial Sequence
<220> FEATURE:
<223> OTHER INFORMATION: MAHs: synthetic degenerate oligonucleotide
<220> FEATURE:
<221> NAME/KEY: misc_feature
<222> LOCATION: (1)..(20)
<223> OTHER INFORMATION: PCR primer element
<220> FEATURE:
<221> NAME/KEY: modified_base
<222> LOCATION: (6)..(6)
<223> OTHER INFORMATION: "n" : I
<220> FEATURE:
<221> NAME/KEY: modified_base
<222> LOCATION: (18)..(18)
<223> OTHER INFORMATION: "n" : I

<400> SEQUENCE: 8
atggcncayg aytayytngt                                              20

<210> SEQ ID NO 9
<211> LENGTH: 20
<212> TYPE: DNA
<213> ORGANISM: Artificial Sequence
<220> FEATURE:
<223> OTHER INFORMATION: IGTa: synthetic degenerate oligonucleotide
<220> FEATURE:
<221> NAME/KEY: misc_feature
<222> LOCATION: (1)..(20)
<223> OTHER INFORMATION: PCR primer element
<220> FEATURE:
<221> NAME/KEY: modified_base
<222> LOCATION: (3)..(3)
<223> OTHER INFORMATION: "n" : I
<220> FEATURE:
<221> NAME/KEY: modified_base
<222> LOCATION: (9)..(9)
<223> OTHER INFORMATION: "n" : I
<220> FEATURE:
<221> NAME/KEY: modified_base
<222> LOCATION: (12)..(12)
<223> OTHER INFORMATION: "n": I
<220> FEATURE:
<221> NAME/KEY: modified_base
<222> LOCATION: (15)..(15)
<223> OTHER INFORMATION: "n" : I
<220> FEATURE:
<221> NAME/KEY: modified_base
<222> LOCATION: (18)..(18)
<223> OTHER INFORMATION: "n" : I

<400> SEQUENCE: 9
acnggrtang cngtnccnat                                              20
```